US00PP10414P

United States Patent [19]

Bergman

[11] Patent Number: Plant 10,414

[45] Date of Patent: May 26, 1998

[54] AZALEA PLANT NAMED MEMORIES

[75] Inventor: Wendy R. Bergman, Lehigh Acres, Fla.

[73] Assignee: Yoder Brothers, Inc., Barberton, Ohio

[21] Appl. No.: 807,402

[22] Filed: Feb. 27, 1997

[51] Int. Cl.[6] ..... A01H 5/00

[52] U.S. Cl. ..... Plt./56

[58] Field of Search ..... Plt./55, 56

*Primary Examiner*—James R. Feyrer

*Attorney, Agent, or Firm*—C. A. Whealy

[57] ABSTRACT

A new and distinct cultivar of Azalea plant named 'Memories', characterized by its dark green leaves that do not abscise during the cooling and forcing periods; uniform and symmetrical plant habit; numerous and large single coral-colored flowers with undulating petal margins that give the flower a ruffled appearance; excellent postproduction longevity with flowers lasting up to four weeks in an interior environment; and very good resistance to the fungal pathogen Cylindrocladium.

1 Drawing Sheet

The present invention relates to a new and distinct cultivar of Azalea, botanically known as *Rhododendron hybrida*, an evergreen greenhouse-forcing type, and hereinafter referred to by the cultivar name Memories.

The new cultivar is a product of a planned breeding program conducted by the inventor in Alva, Fla. The objective of the breeding program is to create new Azalea cultivars having good plant habit, uniform flowering, numerous flowers, good foliage retention during the cooling and forcing periods, and good postproduction longevity.

The new cultivar originated from a cross made by the inventor in Alva, Fla. of the non-patented commercial cultivar Alaska as the female, or seed, parent with the unnamed proprietary seedling selection number 0227 as the male, or pollen, parent. Compared to plants of the white-flowered cultivar Alaska, plants of the new Azalea have more controlled and uniform plant habit, longer postproduction longevity (usually 8 to 10 days longer), and larger flowers. Compared to plants of the double hose-in-hose flower-type seedling selection number 0227, plants of the new Azalea have more uniform plant habit and darker coral flower color.

The cultivar Memories was discovered and selected by the inventors as a flowering plant within the progeny of the stated cross in a controlled environment in Alva, Fla., in Jan., 1992. The selection of this plant was based on its desirable flower color, good postproduction longevity, and uniform plant habit and flowering.

Asexual reproduction of the new cultivar by terminal cuttings taken in a controlled environment in Alva, Fla., has shown that the unique features of this new Azalea are stable and reproduced true to type in successive generations.

The cultivar Memories has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Memories'. These characteristics in combination distinguish 'Memories' as a new and distinct cultivar:

1. Dark green leaves that do not abscise during the cooling and forcing periods.
2. Uniform and symmetrical plant habit.
3. Numerous and large single coral-colored flowers with undulating petal margins that give the flower a ruffled appearance.
4. Excellent postproduction longevity with flowers lasting up to four weeks in an interior environment.
5. Very good to excellent resistance to the fungal pathogen Cylindrocladium.

Plants of the new Azalea can be compared to plants of the commercial cultivar Champagne (U.S. Plant Pat. No. 9,131). However, in side-by-side comparisons conducted in Alva, Fla., plants of the new Azalea differ from plants of the cultivar Champagne in the following characteristics:

1. Plants of the new Azalea are larger than plants of the cultivar Champagne.
2. Leaves of plants of the new Azalea are thicker and more round than leaves of plants of the cultivar Champagne.
3. Flowers of plants of the new Azalea are much larger than flowers of plants of the cultivar Champagne.
4. Plants of the new Azalea have more flowers than plants of the cultivar Champagne.
5. Plants of the new Azalea last about four weeks which is about five to seven days longer than plants of the cultivar Champagne.

The accompanying colored photograph illustrates the overall appearance of the new cultivar, showing the colors as true as it is reasonable possible to obtain in colored reproductions of this type. The photograph comprises a side perspective view of typical plant of 'Memories'. Flower and foliage colors in the photograph may appear different from the actual colors due to light reflectance.

The aforementioned and following observations, measurements, values, and comparisons describe plants grown in Alva, Fla., in 12.5-cm containers with day temperatures ranging from 16 to 35C and night temperatures ranging from 10 to 24C. Plants were grown under 50 percent polypropylene shade cloth reducing ambient light levels to about 4,000 to 5,000 footcandles. After flower bud development, plants were cooled at 3 to 5C for six weeks to break flower bud dormancy. Plants were subsequently forced into flower under commercial conditions in a polyethylene-covered greenhouse.

In the following description, color references are made to The Royal Horticultural Society Colour Chart except where general terms of ordinary dictionary significance are used.

Botanical classification:

*Botanical.*—*Rhododendron hybrida* cv. Memories.

*Commercial.*—Evergreen greenhouse-forcing type Azalea.

*Parentage:*

*Male or pollen parent.*—Unnamed proprietary *Rhododendron hybrida* seedling selection number 0227.

*Female or seed parent.*—*Rhododendron hybrida* cv. Alaska (not patented).

Propagation:

*Type.*—By terminal cuttings.

*Time to develop roots.*—Summer: About 56 days at temperature of 24° C. Winter: About 70 days at temperature of 24° C.

*Rooting habit.*—Moderately vigorous and finely-branched.

Plant description:

*Plant form and growth habit.*—Perennial, evergreen, outwardly spreading, inverted triangle, uniform and symmetrical plant habit. Moderate vigor.

*Branching habit.*—Moderate branching, about three lateral branches develop after removal of terminal apex.

*Plant height, soil level to top of flowers.*—About 23 cm.

*Plant diameter, area of spread.*—About 40 cm.

*Lateral branch description.*—Length: About 9 cm. Diameter: About 4.5 mm. Color: 175B. Texture: Sparsely pubescent.

Foliage description:

*Arrangement.*—Alternate, single.

*Leaf size, largest leaves.*—Length: About 4.5 cm. Width: About 2.5 cm.

*Leaf shape.*—Elliptic. *Leaf apex.*—Mucronate. *Leaf base.*—Attenuate. *Margin type.*—Entire. *Texture.*—Leathery, pubescent on both surfaces. *Color.*—Young foliage, upper surface: Darker than 147A. Young foliage, lower surface: Greener than 146B. Mature foliage, upper surface: Darker than 147A. Mature foliage, lower surface: Greener than 146B. Venation, upper surface: 147A. Venation, lower surface: 146C.

*Petiole.*—Length: About 1 cm. Diameter: About 3 mm. Color: 146C.

Flower description:

*Natural flowering season.*—Spring after sufficient cool period.

*Flower arrangement.*—Flowers arranged singly at terminals with usually about five flowers per terminal. Flowers face outward. Freely flowering.

*Flower appearance.*—Star-shaped single. Soft coral-colored petals. Flowers persistent.

*Flower diameter.*—About 9 cm.

*Postproduction longevity.*—Under interior conditions, plants maintain good flower substance for about four weeks.

*Flower bud.*—Rate of opening: About three days depending on temperatures. Length: About 2.3 cm. Diameter: About 1 cm. Shape: Ovoid. Color: 48A/52D.

*Petals.*—Appearance: Iridescent, satiny. Texture: Smooth. Arrangement: Single. Corolla consists of five fused petals. Shape: Spatulate with rounded apex. Margin: Entire, undulating edge gives a ruffled appearance. Size: Length: About 5.5 cm. Width: About 4.5 cm. Color: When opening, upper and lower surfaces: 48A/52D with white at base. Fully opened, upper and lower surfaces: 48A/52D with white at base.

*Sepals.*—Appearance: Five petaloid sepals fused into a irregularly-shaped calyx. Texture; Pubescent. Shape: Variable. Color, upper and lower surfaces: 144A and 48A/52D at apices.

*Peduncles.*—Length: About 1.2 cm. Angle: Upright. Strength: Flexible. Color: 144A/144B.

*Reproductive organs.*—Androecium: Stamen number: Five. Stamen length: About 2.75 cm. Anther shape: Oblong. Anther size: About 3 mm. Anther color: Purple. Amount of pollen: Moderate. Pollen color: Golden orange. Gynoecium: Pistil number: One. Pistil length: About 3.5 cm. Stigma shape: Rounded. Stigma color: Cream. Style length: About 2.8 cm. Style color: 38A to white at base. Ovary color: Light green, very pubescent.

Disease resistance: No known Azalea diseases observed to date on plants grown under commercial greenhouse conditions. The new Azalea has demonstrated very good to excellent resistance to the fungal pathogen Cylindrocladium.

Seed production: Seed production has not been observed.

It is claimed:

1. A new and distinct Azalea plant named 'Memories', as illustrated and described.

* * * * *

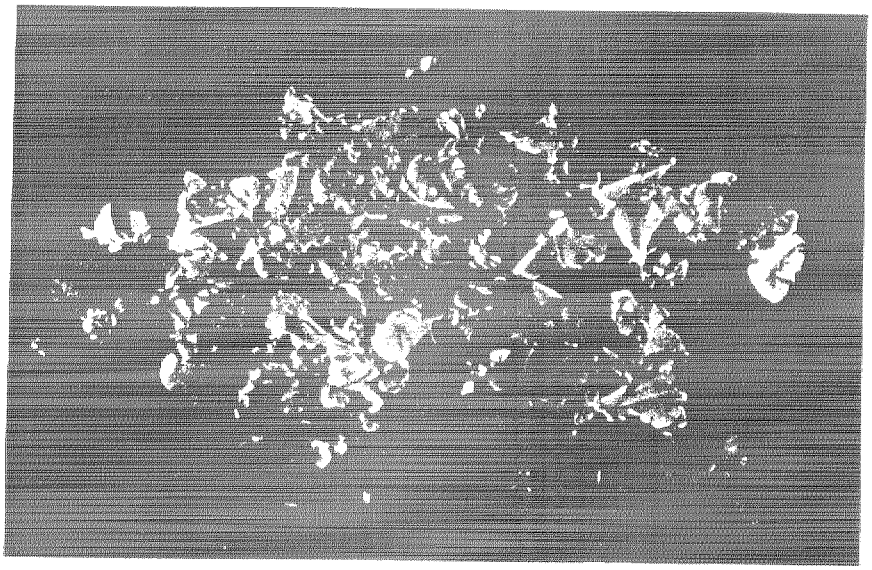

PLT-239 SR
C5203 OR PP 010,414
U.S. Patent May 26, 1998 Plant 10,414